United States Patent [19]

Graether

[11] Patent Number: 5,267,553
[45] Date of Patent: Dec. 7, 1993

[54] PUPIL EXPANDER AND METHOD OF USING THE SAME

[76] Inventor: John M. Graether, 611 Elmwood Dr., Marshalltown, Iowa 50158

[21] Appl. No.: 836,361

[22] Filed: Feb. 18, 1992

[51] Int. Cl.[5] .......................... A61B 17/02; A61F 2/14
[52] U.S. Cl. ...................................... 128/20; 606/107; 623/4
[58] Field of Search .................. 606/107, 166; 128/20, 128/3; 623/4

[56] References Cited

U.S. PATENT DOCUMENTS

| | | | |
|---|---|---|---|
| 2,812,758 | 11/1957 | Blumenschein | 128/20 |
| 3,807,393 | 4/1974 | McDonald | 128/20 |
| 4,387,706 | 6/1983 | Glass | 128/20 |
| 4,452,235 | 6/1984 | Reynolds | 623/5 |
| 4,782,820 | 11/1988 | Woods | 128/20 |
| 5,163,419 | 11/1992 | Goldman | 623/4 X |
| 5,188,125 | 2/1993 | Kilmer et al. | 606/166 X |

Primary Examiner—Richard J. Apley
Assistant Examiner—Donna L. Maraglio
Attorney, Agent, or Firm—Zarley, McKee, Thomte, Voorhees & Sease

[57] ABSTRACT

A pupil expander has an elongated plastic resilient hollow ring which is C-shaped in cross section, and formed into a partial circle. The ends of the ring member have perforated tabs thereon, and are connected together by a strap. The pupil expander is compressed into an elongated shape. Forcep tips are inserted into the ends of the ring member to hold the ring member during insertion of the expander into the anterior chamber of the eye through an incision in the eye outside the location of the iris. An elongated tool can be inserted into the eye if required to facilitate the engagement of the ring member with the iris. The ring member is allowed to gradually expand and engage the inner periphery of the iris and to be received within an elongated outer peripheral opening in the ring member as the forcep tips are gradually withdrawn. The pupil expander is removed from the eye by cutting the strap adjacent one of the tabs, grasping the tab adjacent the cut, and longitudinally pulling the expander through the incision through which it was inserted.

7 Claims, 6 Drawing Sheets

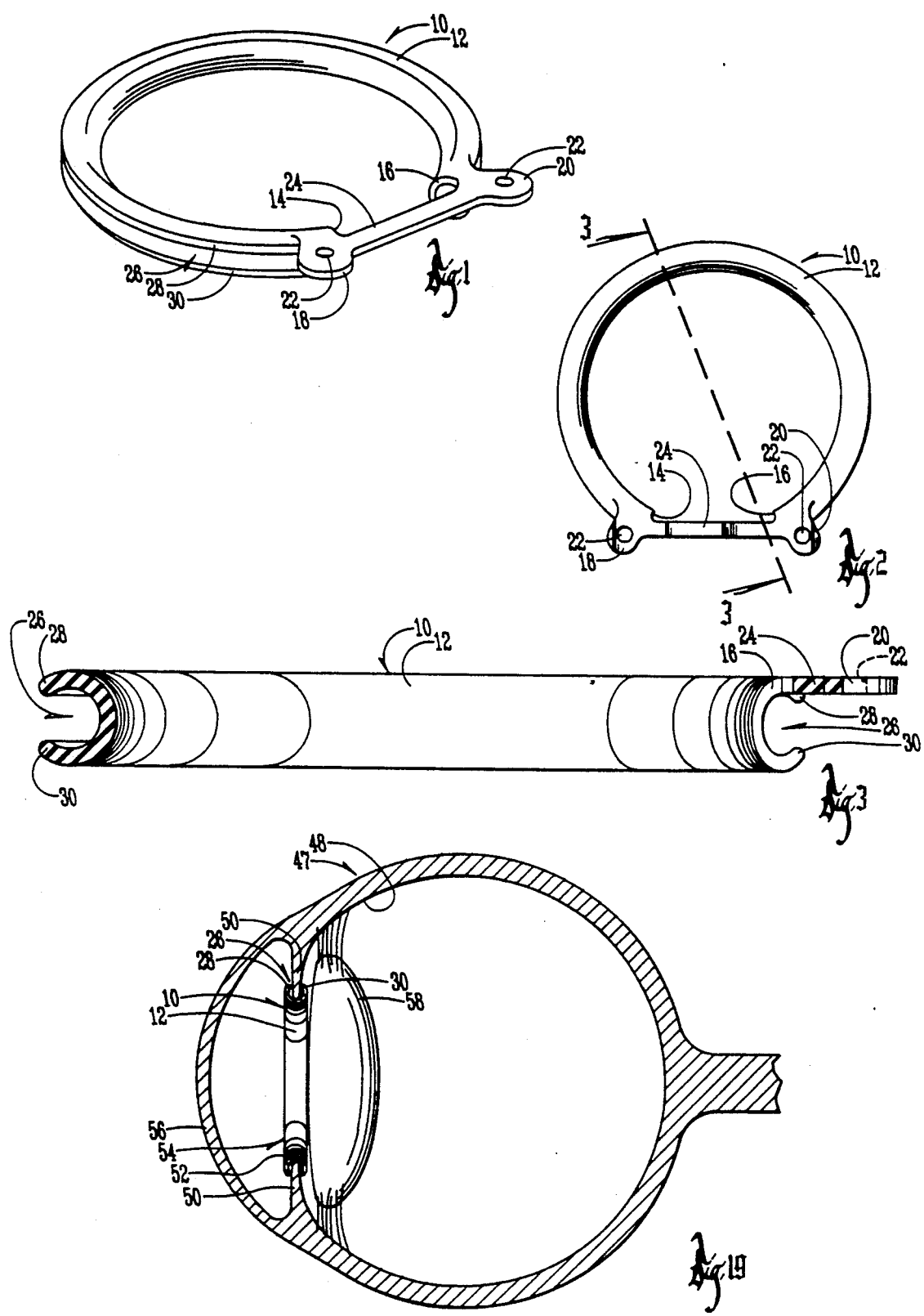

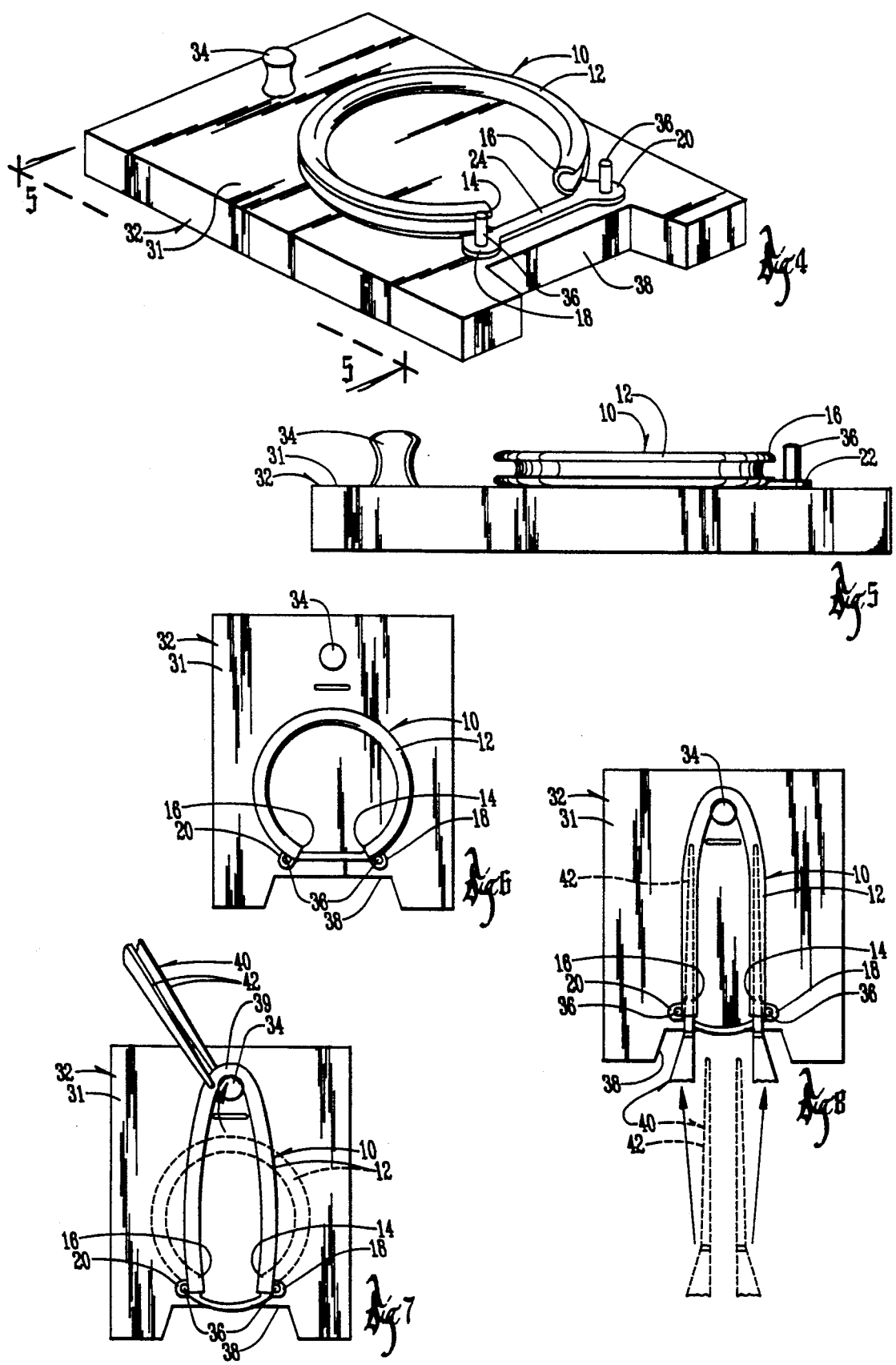

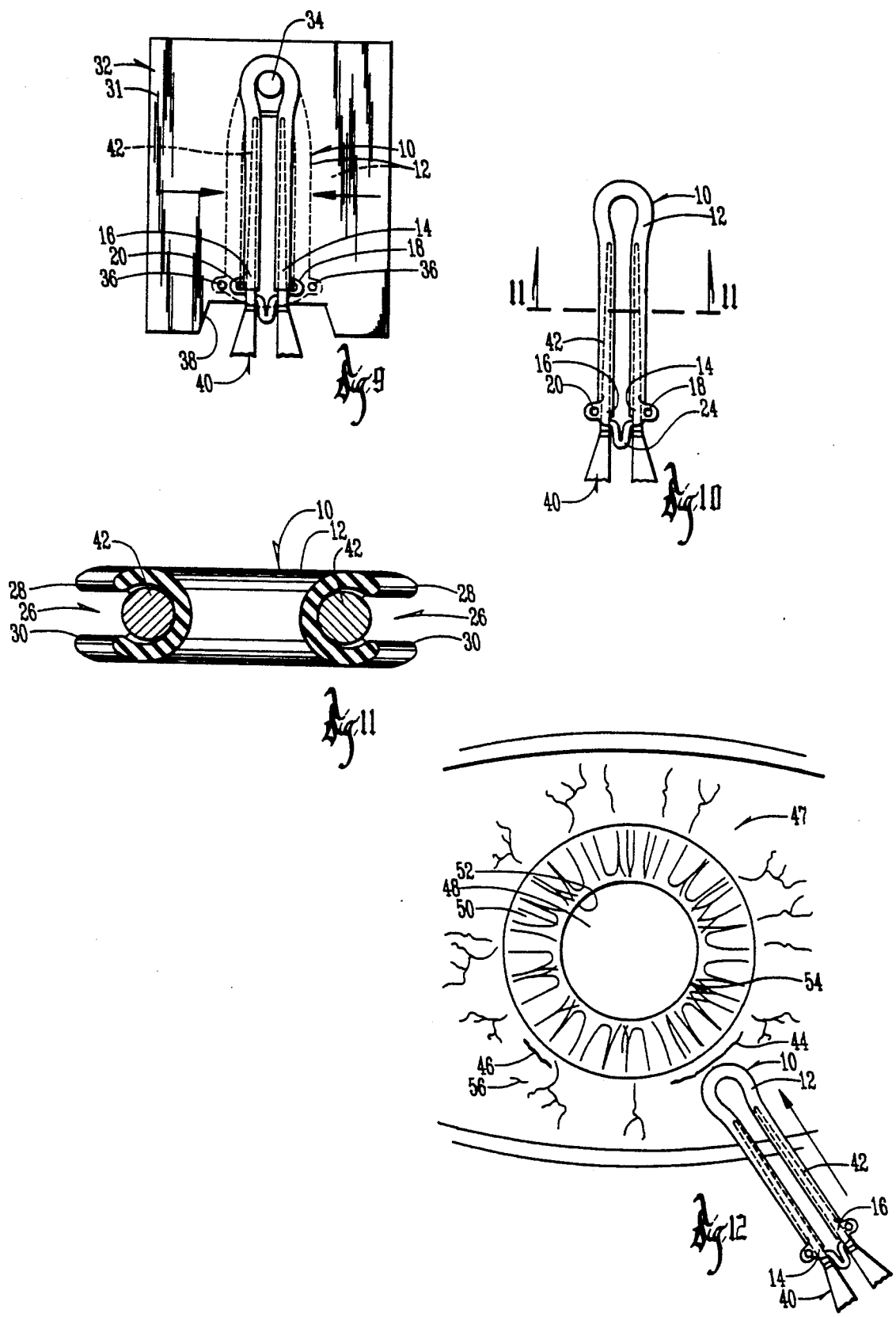

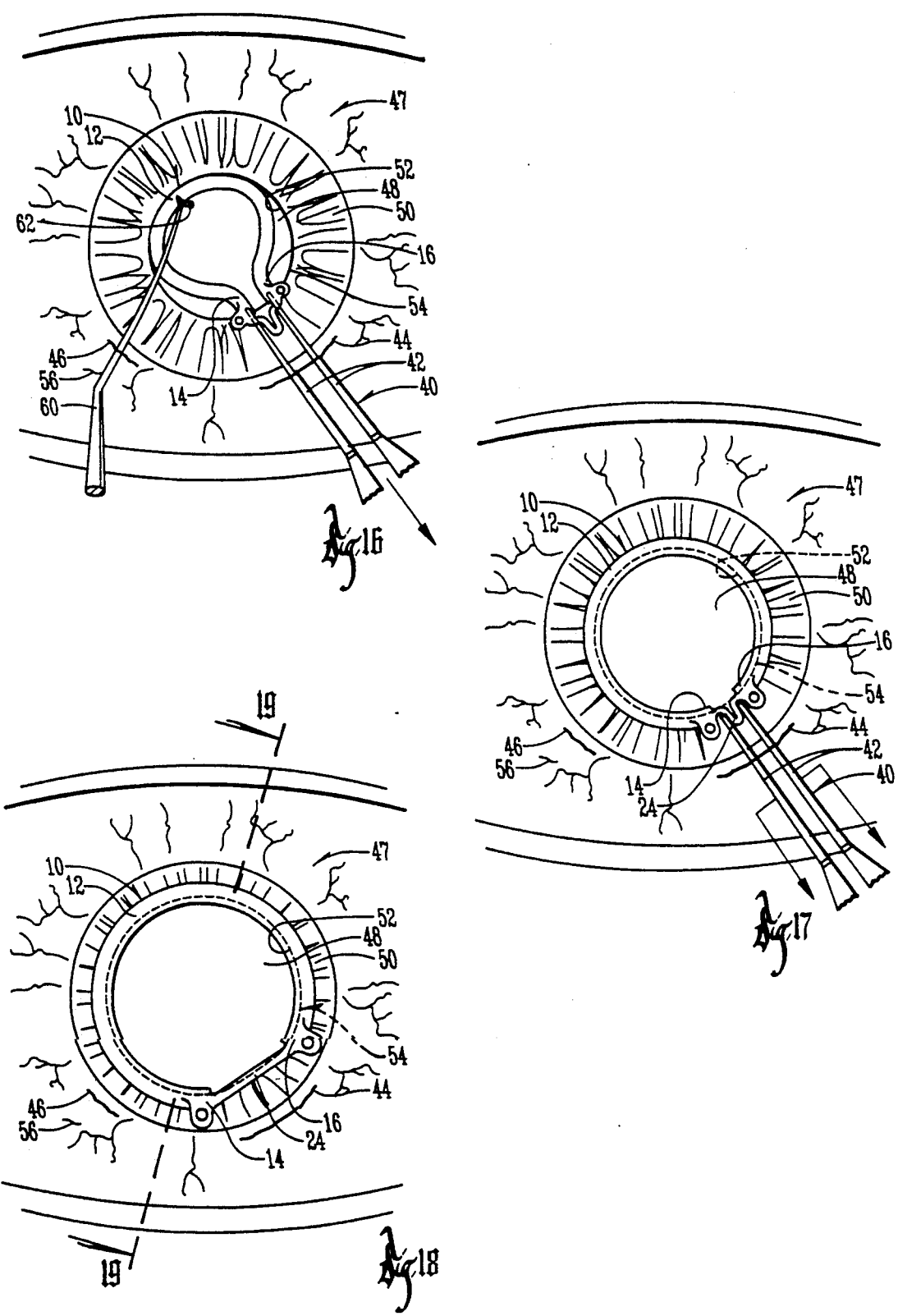

PUPIL EXPANDER AND METHOD OF USING THE SAME

BACKGROUND OF THE INVENTION

Contraction of the pupil during surgery creates substantial difficulty for the surgeon because it inhibits visability and access with respect to the eye during the surgical procedure. For certain procedures, the pupil needs to be enlarged beyond its normal size. Contraction of the pupil during the course of intraocular surgery often takes place. Also, going into surgery, the pupil frequently will not dilate adequately using pharmacologic agents so that surgical maneuvers can be effectively and safely performed. Resistance to dilatation may be due to structural changes in the iris induced by disease such as uveitis, long standing miotic therapy, senile sphincter atrophy, or diseases such as diabetes or pseudoexfoliation of the lens capsule. Various surgical techniques to mechanically enlarge the pupil are not uniformly effective, are time consuming, and often result in permanent defects in the iris sphincter.

Typical prior art devices to accommodate pupil dilation range from being essentially inoperative to being cumbersome, time consuming to insert, and essentially ineffective. Among these devices are those shown in U.S. Pat. Nos. 3,490,455; 4,037,589; 4,257,406; 4,387,706; and 4,782,820.

Therefore, a principal object of this invention is to provide a pupil expander that can be quickly and easily inserted into the eye.

A further object of this invention is to provide a pupil expander that can be quickly and easily removed from the eye at completion of surgery.

A still further object of this invention is to achieve a gradual incremental expansion of the pupil so as to prevent injury to the delicate iris structure during insertion. In addition, this controlled stretching of the pupil to a precisely determined and limited extent may restore the pupil to a more normal and desirable size, improving its function as an iris diaphram.

A still further object of this invention is to prevent the over-stretching of the pupil during the operative maneuvers by limiting its expansion to a precise, predetermined size just large enough to accomplish the intended surgical maneuvers.

A still further object of this invention is to attach the appliance securely to the iris by the clamping effect of its "C" cross section so that the entire pupil aperture created can be transposed in the plane of the iris by gentle lateral pressure on the ring thereby exposing additional fields for surgical maneuvers.

A still further object of this invention is to provide sustained dilation and protection of the pupil margin during prolonged surgical procedures such as training in phacoemulsification. The appliance would also allow re-expansion of the pupil where the pupil constricts during the course of a surgical procedure thereby restoring visibility and surgical access.

A still further object of this invention is to provide an expander which can be made in different sizes depending on the anticipated surgical procedure such as cataract surgery, retinal repair, vitreous surgery, etc.

A still further object of this invention is to provide a pupil expander that will stay in place once it is inserted, and which will not irritate or damage the eye tissues.

A still further object of this invention is to provide a pupil expander which can be easily shipped, stored and otherwise handled and manipulated.

A still further object of this invention is to provide a pupil expander which will provide the surgeon with good visibility of the eye and will not interfere with the surgical procedures.

A still further object of this invention is to provide a pupil expander which will provide a method of inserting the pupil expander of this invention in a quick and safe manner.

These and other objects will be apparent to those skilled in the art.

SUMMARY OF THE INVENTION

The pupil expander of this invention comprises a ring of silicone or other suitable soft plastic tubular material (e.g. Silastic® silicone, Dow Corning, durometer value of about 50) with an outside diameter of 8.2 millimeters and an inside diameter of 7.0 millimeters. The ring has a "C" cross section configuration with a peripheral opening at the outside edge. The ring is incomplete with approximately a 3 millimeter gap to permit surgical maneuvers within it, and that gap is bridged by a strap between the open ends of the ring. There are also two tabs with holes, which are used for manipulation of the device inside and outside the eye.

The method of use of this pupil expander comprises the moving of the pupil expander, which is inserted into the anterior chamber of the eye through a previously prepared scleral incision. The expander is advanced across the anterior chamber until the flared end of the expander engages the iris at a 6 o'clock position. A spatula or lens manipulator is used to hold the expander in place against the iris sphincter while the forceps tips are partially withdrawn. The tips are then closed on the expander, and the tips are advanced into the eye causing the expander to enlarge horizontally engaging additional iris. The tips are then withdrawn an additional millimeter or two, and the above maneuver is repeated until the expander has been advanced onto the sphincter and the pupil has been gradually dilated. When the forceps have been withdrawn until they are opposite the tabs on the expander, the handle is lifted pushing the tips and the contained expander down toward the lens permitting the tabs to come down against the iris and completing the placement of the expander entirely within the pupil.

When the surgical maneuvers are completed, a small scissors is used to cut the silicone strap joining the ends of the pupil expander, and a forceps is used to lift one end of the expander by grasping the tab and moving it toward the center and lifting it to disengage the iris. Once one edge has been disengaged from the sphincter, the expander can simply be pulled from the eye under a layer of viscoelastic material.

BRIEF DESCRIPTION OF THE DRAWINGS

FIG. 1 is a perspective view of the pupil expander of this invention;

FIG. 2 is a plan view thereof shown at a slightly reduced scale;

FIG. 3 is a partial sectional view taken on line 3—3 of FIG. 2;

FIG. 4 is a perspective view of the pupil expander of FIG. 1 mounted on a carrier device;

FIG. 5 is an enlarged scale elevational view as seen on line 5—5 of FIG. 4;

FIG. 6 is a reduced scale plan view of the structure of FIG. 5;

FIG. 7 is a view similar to that of FIG. 6 but shows the position of the pupil expander when it is moved to its elongated position on the carrier device;

FIG. 8 is a plan view similar to that of FIG. 7 but shows schematically the insertion of the forcep thongs into engagement with the pupil expander;

FIG. 9 is a plan view similar to that of FIG. 8 but shows the initial step of the forceps being used to remove the pupil expander from the carrier device;

FIG. 10 shows the pupil expander being fully secured by the forceps after removal from the carrier device;

FIG. 11 is a sectional view taken on line 11—11 of FIG. 10;

FIG. 12 shows the initial step of inserting the pupil expander into the eye;

FIG. 16 is similar to that of FIG. 15 but shows the pupil expander in a subsequent state of expansion within the eye;

FIG. 17 is similar to that of FIG. 16 but shows the pupil expander in a substantially expanded condition just before the forceps are completely removed therefrom;

FIG. 18 is a view similar to that of FIG. 17 showing the pupil expander in its fully expanding condition within the eye;

FIG. 19 is an enlarged scale sectional view taken on line 19—19 of FIG. 18;

DESCRIPTION OF THE PREFERRED EMBODIMENT

Figure 13:
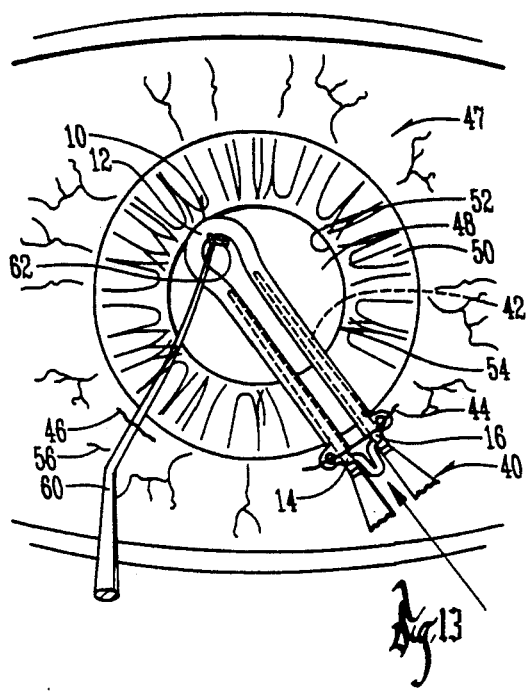
FIG. 13 shows the initial insertion of the pupil expander into the eye just prior to the removal of the forceps.

The pupil expander 10 (FIG. 1) is comprised of a hollow ring member 12 which has opposite ends 14 and 16. Tabs 18 and 20 are formed adjacent the ends 14 and 16, respectively, and each tab has an aperture 22 therein. A strap 24 extends between tabs 18 and 20 to hold the ring member 12 in its circular configuration. It should be noted that the pupil expander 10 is of one-piece integral construction. The ring member 12 is normally in the circular configuration shown in FIGS. 1 and 2. As best shown in FIG. 11, ring member 12 is C-shaped in cross section and has an outer peripheral opening 26 which is adapted to engage the tissue of the eye as will be described hereafter. The peripheral opening 26 is defined by the lip edges 28 and 30 (FIG. 3). The resilient ring member 12 permits the lip edges 28 and 30 to grip the tissue of the eye as the eye tissue enters opening 26 and slightly spreads the lip edges 28 and 30 apart.

With particular reference to FIGS. 4 and 5, a carrier 32 has an upper flat surface 31 with upstanding posts 34 and 36. Post 34 has concave-shaped sides, and the three posts are spaced from each other and form a triangular configuration. The distance between post 34 and the two posts 36 is greater than the normal diameter of ring member 12. Carrier 32 has an indented portion 38 to provide clearance for the forceps during the removal of the pupil expander from the carrier.

The pupil expander is normally packaged and transported on the carrier as shown in FIGS. 1 and 2 wherein the apertures 22 in tabs 18 and 20 are mounted on the posts 36. As will be described hereafter, just prior to being used, the pupil expander is stretched to an elongated condition and is hooked over post 34 as shown in FIG. 7 to create a bight portion 39 at the position of post 34. Forceps 40 with forcep prongs 42 which are circular in cross section are used to manipulate, insert, and remove the pupil expander with respect to the eye as will be described in more detail hereafter.

As shown in FIG. 12, for example, a scleral incision 44 approximately 3.0 millimeters long is made in the eye tissue adjacent the iris and pupil prior to the insertion of the pupil expander 10 into the eye. A second shorter corneal incision 46 is also made to accommodate an additional tool to be described hereafter.

The eye 47 includes anterior chamber 48, iris 50, sphincter 52, pupil 54, cornea 56 and lens 58.

An elongated iris and lens manipulator tool 60 with a hook-shaped tip 62 is adapted for insertion through incision 46 during the procedure for inserting the pupil expander into the eye.

The ring member 12 is comprised of silicone or other suitable soft plastic tubular material having an outside cross sectional diameter of approximately 0.6 millimeters and an inside diameter of approximately 0.34 millimeters with a wall thickness of approximately 0.13 millimeters. With respect to the plan view of the pupil expander 10 in FIG. 2, the ring member 12 has an outside diameter of approximately 8.2 millimeters and an inside diameter of approximately 7.0 millimeters. The length of strap 24 is approximately 3 millimeters.

In operation, the forceps 40 are used to move the pupil expander 10 shown in FIG. 6 to the elongated position shown in FIG. 7. The forcep tips 42 are then moved longitudinally into the ring member 10 through the open ends 14 and 16 as shown by the dotted lines in FIG. 8.

The forceps 40 are then lifted to remove the tabs 18 and 20 from the posts 34 as shown in FIG. 9. The forceps are then raised with respect to the carrier 32 to completely remove the pupil expander 10 from the carrier as shown in FIG. 10. This step normally causes the strap 24 to be collapsed as best shown in FIGS. 9 and 10. The position of the forcep tips 42 within the C-shaped cross sectional structure of ring member 12 is best shown in FIG. 11.

Figure 14:
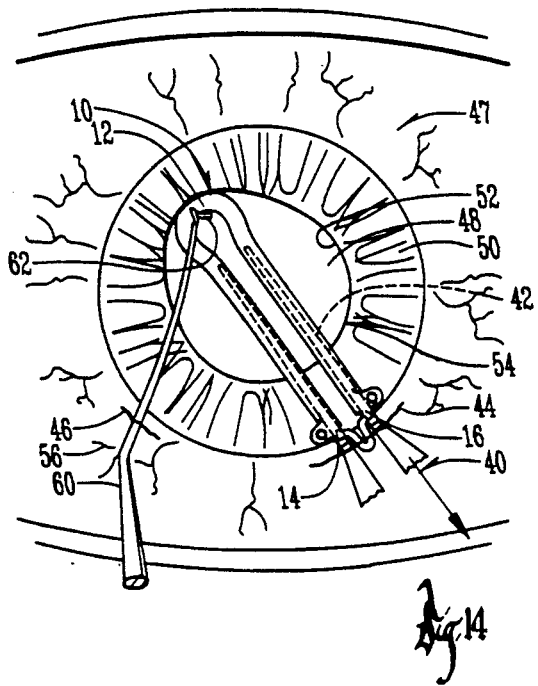
FIG. 14 is a view similar to that of FIG. 13 showing the initial removal of the forceps from the pupil expander.

With the pupil expander in the condition of FIG. 10, the bight portion 39 of the ring member 12 is inserted into incision 44 as shown in FIG. 12. The pupil expander 10 is thereupon moved longitudinally towards the center of the eye as indicated by the arrow in both FIGS. 12 and 13. FIG. 13 shows the position of the pupil expander 10 as moved by the forceps 40 into its maximum position of penetration into the eye wherein the bight portion 39 engages the sphincter 52 which is received within the interior of the ring member 12 at the bight portion 39. Tool 60 can be used as shown in FIGS. 13 and 14 to facilitate the engagement of the bight portion 39 with the sphincter. As shown in FIG. 14, tool 60 is used to maintain the bight portion 39 in connecting relation with the sphincter as the forceps are withdrawn in the longitudinal direction shown by the arrow in FIG. 14.

Figure 15:
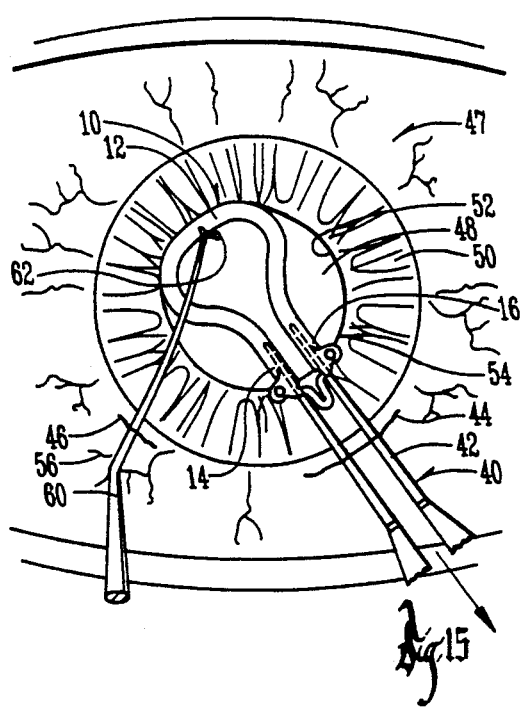
FIG. 15 is a view similar to that of FIG. 14 but shows the forceps substantially removed from the pupil expander and shows the initial expansion of the pupil expander within the eye.

As the forceps are progressively withdrawn from engagement with the pupil expander, the ring member 12 commences to expand within the eye as best shown in FIGS. 15, 16 and 17. As the forcep tips are being withdrawn, the pupil expander 10 is supported by resting the strap 24 on the iris 50. FIG. 17 shows the pupil expander in substantial intimate contact with the sphincter. As soon as the forceps are completely removed from the pupil expander by longitudinally being moved in the direction of the arrow as in FIG. 17, the pupil expander completely expands to the position shown in FIG. 18. This is caused by the expansion of the strap 24 from the crimped position of FIG. 17 to the expanded position of FIG. 18.

Figure 20:
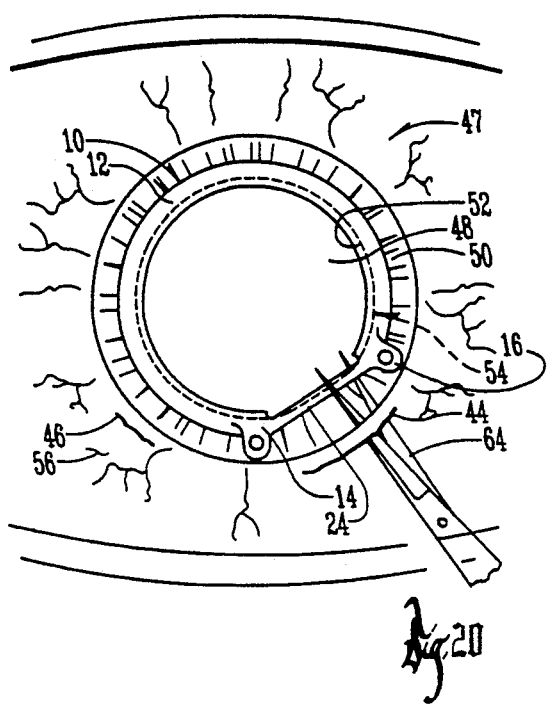
FIG. 20 is a view similar to FIG. 18 but shows the initial step in removing the pupil expander wherein a portion thereof is severed.
Figure 21:
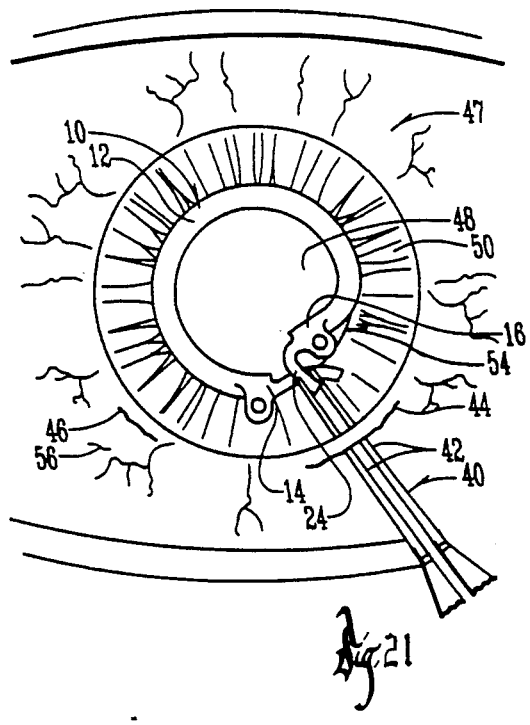
FIG. 21 is a view similar to that of FIG. 20 but shows the next step in removal of the pupil expander wherein forceps are used to grasp one end of the severed pupil expander.
Figure 22:
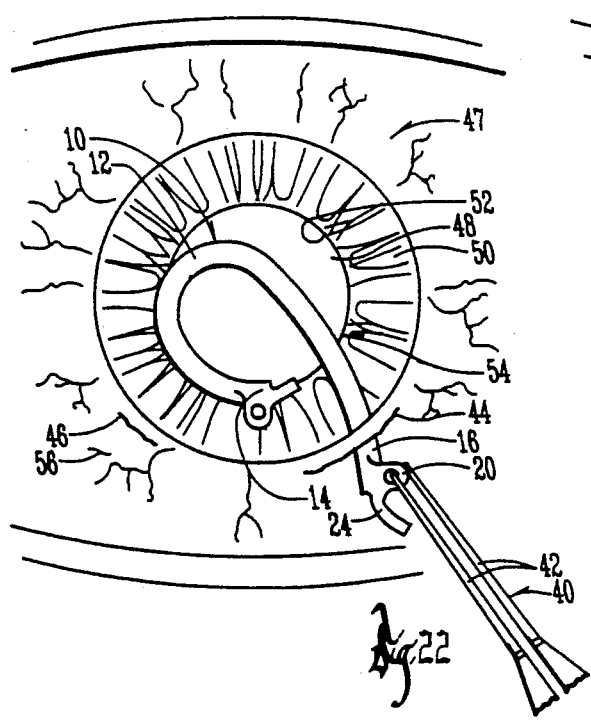
FIG. 22 shows the final step of removal of the pupil expander as the forceps are used to longitudinally pull the severed pupil expander from the eye.

To remove the pupil expander 10 from the eye, scissors 64 (FIG. 20) are inserted through incision 44 to cut strap 24 adjacent one of the tabs 18 or 20. The scissors are then removed from the incision 44 and the forceps are again inserted into the eye as described heretofore. The forceps, as shown in FIG. 21, are used to grasp the tab adjacent the cut strap, and the pupil expander is then pulled from the eye through incision 44 as shown in FIG. 22.

It should be noted that when the forceps remove the pupil expander 10 from the carrier 32 as shown in FIG. 10, the forceps are turned over with the handle upward for inserting the expander into the eye. Prior to inserting the expander, the interior chamber 48 should be filled with a viscoelastic material, and if there are any synechia between the iris 50 and the lens capsule, they should be freed up with a conventional iris retractor.

The expander 10 is advanced across the anterior chamber 48 until the bight 39 of the expander engages the iris at a 6 o'clock position, as generally described above. The tool 60 is used to hold the expander 10 in place against the iris sphincter while the forcep tips are partially withdrawn. The tips 42 are then closed on the expander 10, and the tips are advanced into the eye causing the expander to enlarge horizontally engaging additional portions of the iris sphincter. The tips 42 are then withdrawn an additional millimeter or two, and the above procedures are repeated until the expander 10 has been advanced onto the sphincter and the pupil has been gradually dilated. As generally described heretofore, when the forcep tips 42 have been withdrawn until they are opposite the tabs 18 and 20, the handle on the forceps is lifted pushing the tips and the contained expander 10 down toward the lens 58 permitting the tabs to come down against the iris and completing the placement of expander entirely within the pupil 54.

This maneuver will expand a pupil which is not mechanically rigid or smaller than 4 millimeters in diameter. If the pupil is rigid or fibrosed and cannot be expanded without sphincter rupture, then a sector iridotomy should be cut prior to insertion of the pupil expander 10. The expander can then be inserted in the same manner enlarging the pupil for the desired surgical maneuvers.

The viscoelastic material should be maintained in the anterior chamber 48 during surgical maneuvers such as lens extraction, and the chambers should be refilled if necessary as material is aspirated to prevent the ring member 12 from touching the endothelium.

The pupil expander of this invention and the method of use thereof provides a means of quickly enlarging the pupil and maintaining the pupil at 7 millimeters with minimal trauma to the iris and the sphincter muscle while providing protection to the sphincter during surgical maneuvers. The expander 10 does not interfere with surgical maneuvers within the eye including phacoemulsification of the cataract and implantation of an intraocular lens as well as surgery on the vitreous and retina. Further, the pupil expander 10 can be easily and safely removed at the end of this surgical procedure. It is therefore seen that this invention will achieve at least its stated objectives.

I claim:

1. A pupil expander for use in connection with the inner periphery of the iris of a human eye during human eye surgery, comprising;
    an elongated plastic resilient hollow ring member being arcuate in cross section and having an outer perimeter with an outer peripheral opening adapted to receive the inner perimeter of the iris of the human eye, said ring member having opposite laterally spaced terminal end portions, said ring member having an arcuate length of less than that of a full circle;
    a single strap member integral with and secured to each of said terminal end portions and spanning the space therebetween, and holding said ring member in a substantially circular condition; and a pair of tabs adjacent said terminal end portions;
    said ring member and said strap member being of one piece continuous integral construction.

2. The device of claim 1 wherein an aperture is located in each of said tabs.

3. The device of claim 1 wherein said ring member is C-shaped in cross section and said outer peripheral opening is defined by a pair of spaced lip edges adapted to grip the tissue of the eye as the eye tissue enters said peripheral opening and spreads said lip edges apart.

4. A method of use of a pupil expander for use during eye surgery wherein the pupil expander is comprised of an elongated plastic resilient hollow ring member being arcuate in cross section and having an outer perimeter with an outer peripheral opening to receive the inner perimeter of the iris of a human eye, said ring member having opposite spaced terminal end portions, a strap member integral with and secured to said terminal end portions and spanning the space therebetween and holding said ring member in a substantially circular condition, and a pair of tabs adjacent said terminal end portions, each of said tabs having an aperture therein, comprising: making an incision in the tissue of the eye upon which a surgical procedure is being conducted at a location outside the perimeter of the iris;
    providing a carrier device, said carrier device comprising a pair of posts and a spaced third post;
    compressing the resilient ring member to an elongated shape to form a bight portion within its length, wherein said ring member is compressed to an elongated shape by placing the apertures in said tabs over the pair of carrier posts, and elongating said ring member to form a bight portion, and placing said bight portion over the third carrier post;

longitudinally moving said elongated ring member into the eye through the incision until said bight portion engages the inner periphery of the iris; and permitting said ring member to gradually expand to its normal circular position and to permit said outer peripheral opening to expand, to grip, and to receive the inner periphery of the iris.

5. The method of claim 3 wherein the method further includes the step of providing a pair of forceps having forcep tips, and wherein the pair of forcep tips are placed in opposed portions of said outer peripheral opening to hold said ring member in it selongated shape for insertion into the incision.

6. The method of claim 5 wherein said forcep tips are moved into the eye through the incision, withdrawing said forcep tips from said pupil expander to allow expansion thereof within the eye, and supporting said ring member as said forcep tips are being withdrawn by resting said strap on the iris.

7. A method of use of a pupil expander for use during eye surgery wherein the pupil expander is comprised of an elongated plastic resilient hollow ring member being arcuate in cross section and having an outer perimeter with an outer peripheral opening to receive the inner perimeter of the iris of a human eye, said ring member having opposite spaced terminal end portions, a strap member integral with and secured to said terminal end portions and spanning the space therebetween and holding said ring member in a substantially circular condition, and a pair of tabs adjacent said terminal end portions, comprising:

making an incision in the tissue of the eye upon which a surgical procedure is being conducted at a location outside the perimeter of the iris;

compressing the resilient ring member to an elongated shape to form a bight portion within its length;

longitudinally moving said elongated ring member into the eye through the incision until said bight portion engages the inner periphery of the iris;

permitting said ring member to gradually expand to its normal circular position and to permit said outer peripheral opening to expand, to grip, and to receive the inner periphery of the iris; and further comprising the step wherein said strap member is severed, and one of said tabs is grasped to pull said pupil expander longitudinally out of the eye through the incision.

* * * * *